United States Patent
Laclef et al.

(10) Patent No.: US 10,385,688 B2
(45) Date of Patent: Aug. 20, 2019

(54) WEAR MONITORING SYSTEM FOR MILLING DRUM

(71) Applicant: Caterpillar Paving Products, Inc., Brooklyn Park, MN (US)

(72) Inventors: Sean Robert Laclef, Plymouth, MN (US); Eric Steven Engelmann, Delano, MN (US)

(73) Assignee: Caterpillar Paving Products Inc., Brooklyn Park, MN (US)

( * ) Notice: Subject to any disclaimer, the term of this patent is extended or adjusted under 35 U.S.C. 154(b) by 204 days.

(21) Appl. No.: 15/387,000

(22) Filed: Dec. 21, 2016

(65) Prior Publication Data
US 2018/0171568 A1   Jun. 21, 2018

(51) Int. Cl.
| | |
|---|---|
| E01C 23/12 | (2006.01) |
| E01C 23/088 | (2006.01) |
| E21C 35/18 | (2006.01) |
| B28D 1/18 | (2006.01) |
| G01N 3/58 | (2006.01) |

(52) U.S. Cl.
CPC .............. *E21C 35/18* (2013.01); *B28D 1/188* (2013.01); *E01C 23/088* (2013.01); *E01C 23/127* (2013.01); *G01N 3/58* (2013.01)

(58) Field of Classification Search
CPC .......... E21C 39/00; E21C 27/02; E21C 27/24; E21C 35/04; E01C 23/088; E01C 23/127; E21B 12/02; G01N 3/58
USPC .................................................. 299/1.1, 1.5
See application file for complete search history.

(56) References Cited

U.S. PATENT DOCUMENTS

| | | | | |
|---|---|---|---|---|
| 4,195,946 | A * | 4/1980 | Swisher, Jr. .......... | E01C 11/005 404/75 |
| 4,697,850 | A * | 10/1987 | Tuneblom .............. | B28D 1/188 299/106 |
| 5,842,747 | A * | 12/1998 | Winchester ............ | B28D 1/188 299/87.1 |
| 7,905,682 | B2 | 3/2011 | Holl et al. | |
| 8,128,177 | B2 | 3/2012 | Menzenbach et al. | |
| 2006/0208902 | A1* | 9/2006 | Brey ....................... | B60C 11/24 340/572.8 |
| 2006/0226984 | A1* | 10/2006 | Menke ................... | B65G 33/24 340/572.1 |
| 2013/0035875 | A1* | 2/2013 | Hall ........................ | B02C 18/00 702/34 |
| 2013/0234494 | A1 | 9/2013 | Hall et al. | |
| 2013/0256032 | A1 | 10/2013 | Palmer | |

(Continued)

FOREIGN PATENT DOCUMENTS

DE    4415824 C1    11/1995

*Primary Examiner* — Janine M Kreck
*Assistant Examiner* — Michael A Goodwin
(74) *Attorney, Agent, or Firm* — Finnegan, Henderson, Farabow, Garrett & Dunner, LLP

(57) ABSTRACT

A milling drum is disclosed for use with a cold planer. The milling drum may have a cylindrical body, a flighting plate affixed to an outer surface of the cylindrical body, a base block affixed to the fighting plate and having a first bore, a tool holder disposed in the first bore of the base block and having a second bore, a cutting tool disposed in the second bore of the tool holder, and a paddle affixed to the outer surface of the cylindrical body adjacent the fighting plate. The milling drum may further have a first transmitter coupled to the cutting tool, and a second transmitter coupled to the tool holder.

20 Claims, 3 Drawing Sheets

(56) References Cited

U.S. PATENT DOCUMENTS

| | | | |
|---|---|---|---|
| 2014/0035346 A1* | 2/2014 | Fundakowski | E21C 25/10 299/87.1 |
| 2015/0137579 A1 | 5/2015 | Lachmann et al. | |
| 2015/0300165 A1* | 10/2015 | Marsolek | G06K 7/10425 299/39.4 |
| 2015/0314483 A1* | 11/2015 | Miess | E01C 23/088 299/104 |
| 2015/0322634 A1 | 11/2015 | Stock et al. | |
| 2016/0168991 A1 | 6/2016 | Von der Lippe et al. | |
| 2016/0258119 A1 | 9/2016 | Krolnik et al. | |
| 2016/0369569 A1* | 12/2016 | Bird | E21B 12/02 |
| 2017/0009578 A1* | 1/2017 | Barimani | E21C 25/10 |
| 2017/0159432 A1* | 6/2017 | Lavely | B28D 1/186 |

* cited by examiner

WEAR MONITORING SYSTEM FOR MILLING DRUM

TECHNICAL FIELD

The present disclosure relates generally to a wear monitoring system and, more particularly, to a wear monitoring system for a milling drum.

BACKGROUND

Asphalt-surfaced roadways are built to facilitate vehicular travel. Depending upon usage density, base conditions, temperature variation, moisture levels, and/or physical age, the surfaces of the roadways eventually become misshapen and unable to support wheel loads. In order to rehabilitate the roadways for continued vehicular use, spent asphalt is removed in preparation for resurfacing.

Cold planers, sometimes also called road mills or scarifiers, are used to break up and remove layers of an asphalt roadway. A cold planer typically includes a frame propelled by tracked or wheeled drive units. The frame supports an engine, an operator's station, a milling drum, and conveyors. The milling drum, fitted with cutting tools, is rotated through a suitable interface with the engine to break up the surface of the roadway. The broken up roadway material is deposited by the milling drum onto the conveyors, which transfer the broken up material into haul trucks for removal from the worksite.

The cutting tools are attached to the milling drum by way of tool and/or base blocks. All of these components can wear out over time and/or break during milling operations, necessitating their periodic replacement. Operators typically monitor the wearing and breakage of these components by visually inspecting each component on the milling drum at the beginning and end of each operation and/or during downtime. Depending on the type of material being milled, the cutting depth, and other factors, the cutting tools, tool holders, and/or base blocks may be inspected and replaced every hour, every few hours, every shift, daily, etc. Since a typical milling drum has multiple cutting tools and multiple tool holders and base blocks, the inspection can be labor intensive and time consuming. In addition, the inspection process requires the milling operation to be interrupted. For these reasons, some cutting tools may be replaced prematurely (e.g., out of caution and avoid milling interruption). For the same reasons, the inspection and/or replacement may be avoided or delayed, resulting in collateral component damage. Both situations increase an operating cost of the cold planer.

One attempt to monitor the wearing of a cutting tool is disclosed in U.S. Patent Application Publication No. 2013/0256032 A1 of Palmer that published on Oct. 3, 2013 ("the '032 publication"). In particular, the '032 publication discloses a wear indication system for an abrading tool. The wear indication system includes a sensor, which detects signals emitted by a number of different tags disposed at various locations within a cutting end of the abrading tool. Specifically, the sensor detects changes in signals emitted by the tags, as the tags become dislodged or destroyed during the drilling process. An indication of a wear level of the abrading tool is then determined based on the change in signals, and electronically communicated to an operator of the abrading tool.

While the system of the '032 publication may allow for a wear level of an abrading tool to be monitored, it may be less than optimal. In particular, the system of the '032 publication may cause the abrading tool to wear out more quickly, since each tag occupies space within the tool. That is, voids may be created within the tool in order accommodate the tags, and the voids may reduce a strength of the tool. Additionally, the use of multiple types of tags may increase a complexity and/or cost of the system, making the use of the system prohibitive with machines having a high number of tools.

The wear monitoring system of the present disclosure solves one or more of the problems set forth above and/or other problems in the art.

SUMMARY

In one aspect, the present disclosure is related to a milling drum. The milling drum may include a cylindrical body, a flighting plate affixed to an outer surface of the cylindrical body, a base block affixed to the fighting plate and having a first bore, a tool holder disposed in the first bore of the base block and having a second bore, a cutting tool disposed in the second bore of the tool holder, and a paddle affixed to the outer surface of the cylindrical body adjacent the fighting plate. The milling drum may further include a first transmitter coupled to the cutting tool, and a second transmitter coupled to the tool holder.

In another aspect, the present disclosure is related to a wear monitoring system for a milling drum having a fighting plate affixed to an outer surface, a base block affixed to the fighting plate, a tool holder connected to the base block, a cutting tool connected to the tool holder, and a paddle affixed to the outer surface of the cylindrical body adjacent the fighting plate. The wear monitoring system may include a first transmitter configured to emit a first signal indicative of a status of the cutting tool, a second transmitter configured to emit a second signal indicative of a status of the tool holder, a reader configured to receive the first and second signals, a display, and a controller in communication with the reader and the display. The controller may be configured to selectively cause the display to show a wear status and a connection status of the cutting tool based on a loss of the first signal. The controller may be further configured to selectively cause the display to show a wear status and a connection status of the tool holder based on a loss of the second signal.

In yet another aspect, the present disclosure is related to a method of monitoring wear of a milling drum having a flighting plate affixed to an outer surface, a base block affixed to the fighting plate, a tool holder connected to the base block, a cutting tool connected to the tool holder, and a paddle affixed to the outer surface of the cylindrical body adjacent the flighting plate. The method may include detecting a fighting plate signal, detecting a base block signal, detecting a tool holder signal, detecting a cutting tool signal. The method may also include selectively displaying a wear status and a connection status of the fighting plate, the base block, the tool holder, and the cutting tool based on loss of the fighting plate signal, the base block signal, the tool holder signal, and the cutting tool signal.

DETAILED DESCRIPTION

For the purpose of this disclosure, the term "asphalt" is defined as a mixture of aggregate and asphalt cement. Asphalt cement is a brownish-black solid or semi-solid mixture of bitumens obtained as a byproduct of petroleum distillation. The asphalt cement can be heated and mixed with the aggregate for use in paving roadway surfaces, where the mixture hardens upon cooling. A "cold planer" is defined as a machine used to remove layers of hardened asphalt from an existing roadway. It is contemplated that the disclosed cold planer may also or alternatively be used to remove cement and other roadway surfaces, or to remove non-roadway surface material such as in a reclaiming or mining operation.

Figure 1:
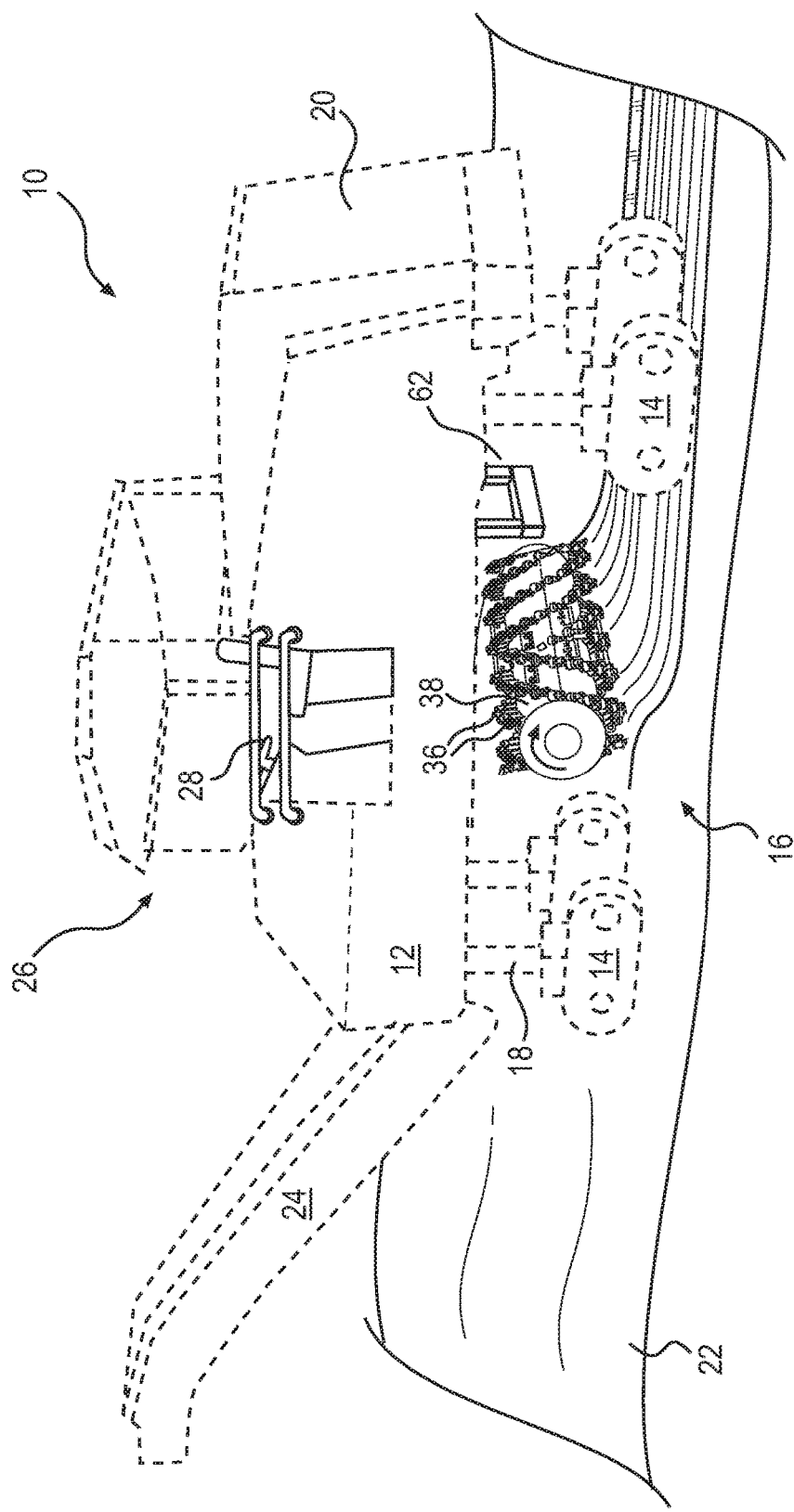
FIG. 1 is an isometric illustration of an exemplary disclosed cold planer.

FIG. 1 illustrates an exemplary cold planer 10. Cold planer 10 may include a frame 12 connected to one or more traction units 14, and a milling drum 16 supported from frame 12 at a general center of cold planer 10 between traction units 14. Traction units 14 may each include either a wheel or a track section that is pivotally connected to frame 12 by an actuator 18. Actuators 18 may be adapted to controllably raise, lower, and/or tilt frame 12 relative to the associated traction units 14. It should be noted that, in the disclosed embodiment, raising and lowering of frame 12 may also function to vary a milling depth of milling drum 16 into a work surface 22. An engine 20 (or other power source) may be configured to electrically, mechanically, hydraulically, and/or pneumatically power traction units 14, milling drum 16, and actuators 18. A conveyor system 24 may be pivotally connected at a leading end to frame 12 and configured to transport material away from milling drum 16 and into a transport vehicle.

Frame 12 may also support an onboard operator station 26. Operator station 26 may house any number of interface devices 28 used to control cold planer 10. In the disclosed example, interface devices 28 may include, among other things, a display 30, and an input device 32 (30 and 32 shown only in FIG. 3). In other embodiments, operator station 26 may be located offboard cold planer 10. For example, operator station 26 may embody a remote control, such as a handheld controller, that an operator uses to control cold planer 10 from anywhere on the worksite. In other embodiments, cold planer 10 may be autonomous and may not include operator station 26. Display 30 may be configured to display data and/or other information to the operator. Input device 32 may be configured to receive instructions from the operator of cold planer 10, for example via one or more buttons, switches, dials, levers, etc.

Milling drum 16 may include components rotated by engine 20 to fragment and remove chunks of asphalt and/or other material from work surface 22. Specifically, milling drum 16 may include one or more rows of cutting tool assemblies 36 operatively connected to an outer cylindrical surface 38. In the disclosed embodiment, three spiraling rows of cutting tool assemblies 36 initiate at each end of milling drum 16 and terminate at a lengthwise center. It should be noted, however, that a greater or lesser number of cutting tool assemblies 36 may be included, if desired.

Figure 2:
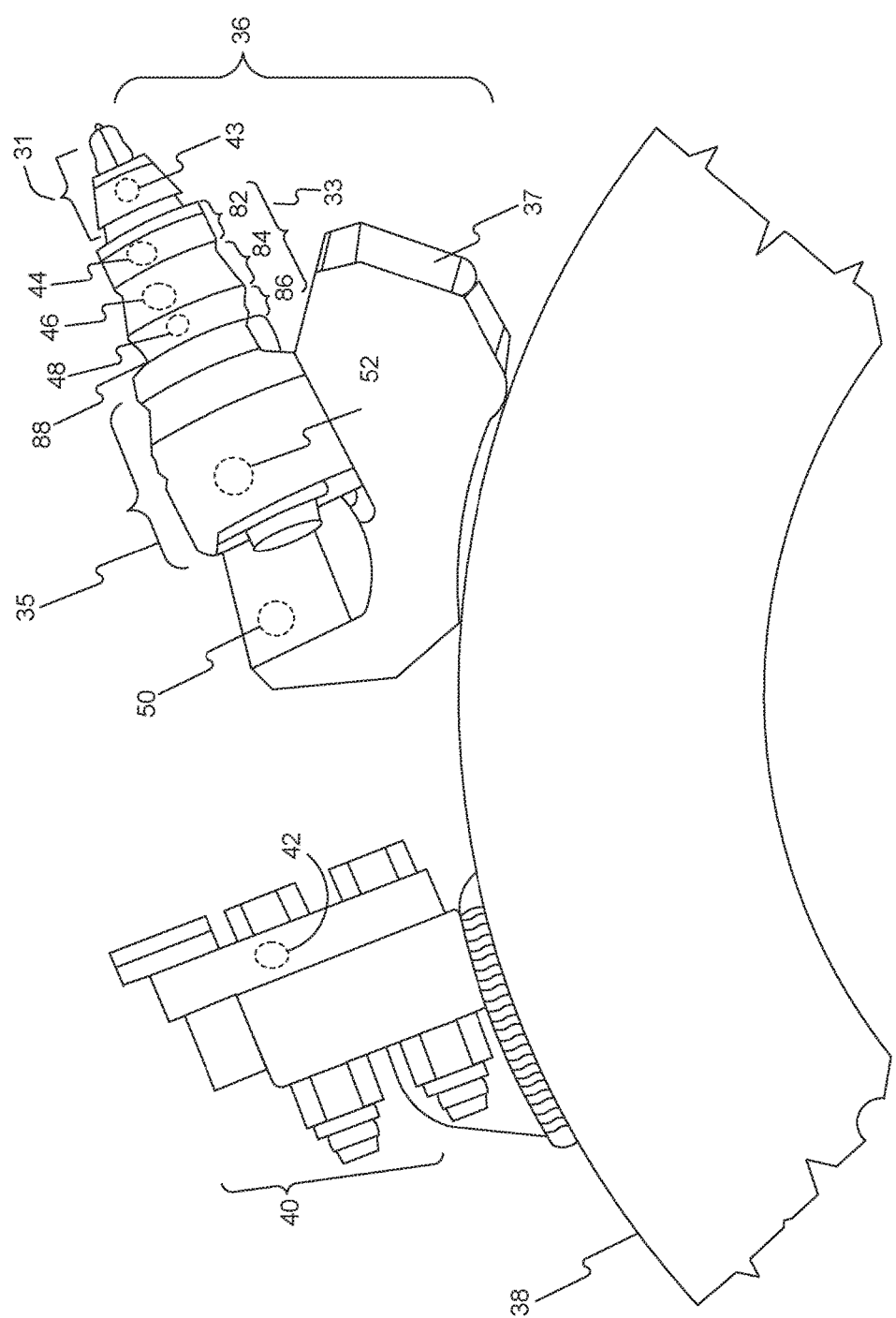
FIG. 2 is an isometric illustration of a portion of the cold planer of FIG. 1.

As shown in FIG. 2, each cutting tool assembly 36 may be formed by a cutting tool 31, a tool holder 33, a base block 35, and a flighting plate 37. Flighting plate 37 may be fixedly connected (e.g., via welding) to outer cylindrical surface 38. Base block 35 may be fixedly mounted onto fighting plate 37 (e.g., by welding). Alternatively, base block 35 and flighting plate 37 may be an integral part. Tool holder 33 may, in turn, may be received within a bore of base block 35. Cutting tool 31 may likewise be received within a bore of tool holder 33. It is contemplated that tool holder 33 and cutting tool 31 may be removably mounted at their corresponding locations (e.g., via threaded fasteners, clips, pins, and/or strategically placed welds), such that these components can be periodically replaced. In some embodiments, cutting tool 31 and tool holder 33 may be integrally formed as a unitary structure that is removably connected to base block 35.

In the embodiment shown in FIG. 2, milling drum 16 may further include one or more paddles 40 connected to outer cylindrical surface 38. For example, paddle 40 may be directly welded to outer cylindrical surface 38. Alternatively, paddle 40 may be removably connected to outer cylindrical surface 38, for example by threaded fasteners, clips, pins, etc., such that paddle 40 may be periodically replaced. Paddle 40 may function to direct ground-up road materials onto a conveyor for disposal at a location remote from milling drum 16.

Cutting tool 31, as seen extending beyond a distal end of tool holder 33 in FIG. 2, may generally have a narrow tip configured to pierce work surface 22 and break up material. During operation, the cutting depth of milling drum 16 may be set by the operator such that the tip of cutting tool 31 penetrates work surface 22 without causing tool holder 33, base block 35 and/or fighting plate 37 to directly engage work surface 22. Thus, cutting tool 31 may generally experience more wear and be replaced more often than the other components. Cutting tool 31 may be replaced when a monitored wear of cutting tool 31 exceeds a threshold level.

Tool holder 33 may be divided into virtual segments, including a top portion 82, a middle portion 84, and a lower portion 86. Each of these portions may be located axially to one side (e.g., an exposed side) of a circumferential groove 88 with lower portion 86 being closest to base block 35. Top portion 82, middle portion 84, and lower portion 86 may all wear down during milling operations due to their exposure to the abrasive environment of milling drum 16. Circumferential groove 88 may be considered as a wear threshold of tool holder 33. In particular, when no fragment of top portion 82, middle portion 84, and lower portion 86 can be seen as extending beyond circumferential groove 88, tool holder 33 may benefit from replacement.

Base block 35, fighting plate 37, and paddle 40 may each generally be more difficult to replace than cutting tool 31 and tool holder 33. For example, these components may need to be torched off and welded back on. Accordingly, these components may generally be replaced only when they are completely missing.

To help automatically detect which component of milling drum 16 may be missing, or to evaluate a wear rate or severity of each component, a plurality transmitters or sensors may be disposed on or inside each component of milling drum 16. For example, as shown in FIG. 2, to help detect when wear of cutting tool 31 exceeds its associated wear threshold, at least one transmitter 43 may be disposed within the tip end of cutting tool 31. In this configuration, transmitter 43 may be a sacrificial component that emits a signal as long as it remains intact (e.g., until the wear of cutting tool 31 exceed the wear threshold). As cutting tool 31 wears, transmitters 43 may become exposed, damaged or lost, and stop emitting signals. Transmitter 43 may be disposed within cutting tool 31 by, for example, drilling a hole into cutting tool 31, inserting transmitter 43 into the hole, and filling the hole with an epoxy or another material. The depth of the drilled hole (and corresponding location of transmitter 43) may be a depth at which signals emitted by transmitter 43 are able to be detected. Namely, signals emitted by transmitter 43 should be detected during normal operation of milling drum 16.

At least one transmitter may also be disposed inside or on an outer surface of each portion of tool holder 33. For example, a first transmitter 44 may be disposed on top portion 82; a second transmitter 46 may be disposed on middle portion 84; and a third transmitter 48 may be disposed on lower portion 86. Transmitters 44-48 may be disposed within tool holder 33 by, for example, drilling holes into tool holder 33 for each transmitter, inserting each transmitter into the holes, and filling the holes with an epoxy or another material. The depths of the drilled holes (and corresponding locations of transmitters 44-48) may be depths at which signals emitted by transmitters 44-48 are able to be detected. Namely, signals emitted by transmitters 44-48 should be detected during normal operation of milling drum 16.

Alternatively, transmitters 44-48 may be fixed to outer surfaces of tool holder 33, for example by an adhesive It is understood that other ways of disposing transmitters 44, 46, and 48 within tool holder 33 may be possible.

Regardless of how transmitters 44-48 are mounted to tool holder 33, a wear rate of tool holder 33 may be evaluated based on the signals generated by (and/or the termination of signal receipt from) transmitters 44-48. For example, during wear of tool holder 33, transmitter 44 in top portion 82 may be destroyed and stop emitting signals after a first period of time, and then transmitter 46 in middle portion 84 may be destroyed and stop emitting signals after a second period of time following the first period of time. Thus a wear rate of tool holder 33 may be estimated by, for example, dividing an unworn or new axial length of top portion 82 and middle portion 84 by a sum of the first and second periods of time. Further, by detecting which of transmitters 44-48 in a particular tool holder 33 are no longer generating signals, a wear severity of that tool holder 33 may be evaluated. For example, a loss of signal from transmitter 44 in top portion 82 may indicate a low wear severity; a loss of signal from transmitter 46 in middle portion 84 may indicate a medium wear severity; and loss of signal from transmitter 48 in lower portion 86 may indicate a high wear severity and a need to replace tool holder 33. In addition, a sudden loss of signal from two or more of transmitters 44-48 within a particular tool holder 33 may indicate a complete breakoff of that tool holder 33.

Also as shown in FIG. 2, base block 35, fighting plate 37, and paddle 40 may each have at least one transmitter disposed inside or on an outer surface thereof. For example, a transmitter 52 may be disposed in base block 35; a transmitter 50 may be disposed in fighting plate 37; and a transmitter 42 may disposed in paddle 40. Loss of signal from any of these transmitters may indicate that the corresponding components may have broken off or broken away from milling drum 16.

The various transmitters associated with the components of milling drum 16 may be configured differently or the same. That is, the transmitters may be the same or different types. For example, transmitter 43 disposed in cutting tool 31 may be a radio frequency identification device (i.e., an RFID) tag, but transmitters 44, 46 and 48 disposed on tool holder 33 may be another type.

Each transmitter may be configured to emit a unique identification signal that is associated with each corresponding component of milling drum 16. For example, transmitter 43 may emit a signal indicating it is associated with a cutting tool 31, associated with a particular cutting tool 31, and/or associated with a cutting tool 31 positioned at a particular location on milling drum 16. In addition, in one embodiment, the unique signal generated by transmitter 43 may link a particular cutting tool 31 to a particular tool holder 33, base block 35, and flighting plate 37 (e.g., to a particular tool assembly 36). In another embodiment, the signal generated by all transmitters of a particular tool assembly 36 may have the same identification signal.

Referring again to FIG. 1, cold planer 10 may include a reader 62 that is configured to detect the signals emitted by each transmitter disposed within each component of milling drum 16 (referring to FIG. 2). Reader 62 may be, for example, an RFID tag reader. It is understood, however, that reader 62 may be another type of reader configured to detect different types of signals, if desired. Reader 62 may be positioned within a distance of milling drum 16 that allows the signals from each transmitter of milling drum 16 to be detected. For example, reader 62 may be connected to cold planer 10 at a location adjacent milling drum 16. Although reader 62 is shown in FIG. 1 as being connected to frame 12, reader 62 may alternatively be connected to other components of cold planer 10, if desired.

Figure 3:
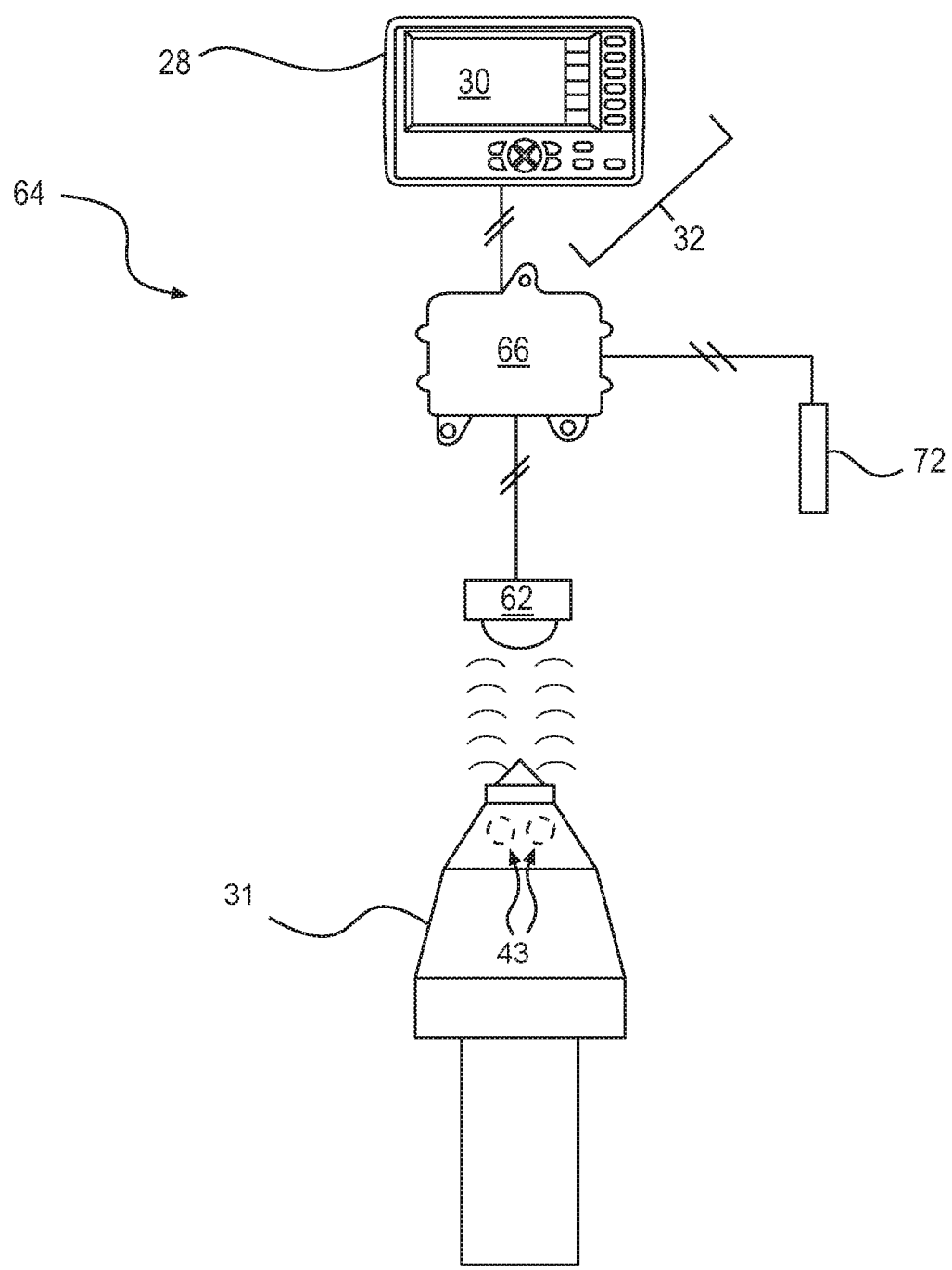
FIG. 3 a diagrammatic illustration of an exemplary disclosed wear monitoring system that may be used with the cold planer of FIG. 1.

Referring to FIG. 3, a wear monitoring system 64 ("system") may be associated with cold planer 10 and include elements that cooperate to determine when each component of milling drum 16 exceeds the wear threshold, breaks, or becomes disconnected from milling drum 16 (referring to FIG. 1) based on the signals emitted by the different transmitters discussed above. Monitoring system 64 may include, among other things, interface devices 28, the different transmitters, reader 62, and a controller 66 electronically connected with each of the other elements. Reader 62 may detect the signals emitted by each transmitter of milling drum 16, and communicate the signals to controller 66. Based on the signals received from reader 62, controller 66 may determine and store in memory information about the different components of milling drum 16. Controller 66 may also generate warnings based on the signals, and show the warnings to the operator of cold planer 10 via display 30. It should be noted that, although FIG. 3 shows a single cutting tool 31, it should be noted that monitoring system 64 may interact in the same way with all of the transmitter-equipped components of milling drum 16 (referring to FIG. 2). In addition, controller 66 may be further in communication with an external computing network, including, but not limited to, a local computing network, a wide computing network, an extranet, the Internet, and/or the Internet of things. Controller 66 may send collected information via the external computing network to, for example, a back office, for further analysis of the collected information (e.g., online remote diagnostics of milling drum 16). Further, replacement components of milling drum 16 may also be ordered (e.g., automatically based on signals from transmitters) and repairs scheduled via the external computing network in advance of the repairs being needed.

Controller 66 may embody a single microprocessor or multiple microprocessors that include a means for monitoring operator and transmitter input, and responsively adjusting operational characteristics of cold planer 10 based on the input. For example, controller 66 may include a memory, a secondary storage device, a clock, and a processor, such as a central processing unit or any other means for accomplishing a task consistent with the present disclosure. Numerous commercially available microprocessors can be configured to perform the functions of controller 66. It should be appreciated that controller 66 could readily embody a general machine controller capable of controlling numerous other machine functions. Various other known circuits may be associated with controller 66, including signal-conditioning circuitry, communication circuitry, and other appropriate circuitry. Controller 66 may be further communicatively coupled with an external computer system, instead of or in addition to including a computer system, as desired.

Controller 66 may be configured to determine when each component of milling drum 16 is connected to milling drum 16 (referring to FIGS. 1 and 2) based on signals emitted by the associated transmitter(s). That is, controller 66 may determine that a particular component is connected to milling drum 16 when reader 62 detects a signal indicative of an ID associated with that component. Controller 66 may automatically record this connection into its memory, along with the unique identification signal(s) of the component.

In other embodiments, each new component connected to milling drum 16 may be manually logged into the memory of controller 66 by the operator or a technician. For example, monitoring system may include a scanning device (not shown) that communicates with controller 66 and is configured to detect and/or assign an ID to the unique signal emitted by each transmitter before and/or while the associated component is being connected to milling drum 16. Alternatively, the IDs may be entered via input device 32 and communicated to controller 66. Further alternatively, IDs may be automatically logged into the memory of controller 66 via the external computing network, for example from a database on which information about the new component is stored.

After a new component is connected to milling drum 16, controller 66 may be configured to monitor the new component and determine when the associated signal(s) from the corresponding transmitter(s) are lost (i.e., when the signal(s) are no longer detected by reader 62). For example, when a signal emitted by a transmitter 50 associated with a particular flighting plate 37 is lost, controller 66 may conclude that the particular fighting plate 37 has broken away from milling drum 16 or is worn or damaged and requires replacement. In this instance, controller 66 may generate a first warning recommending replacement of the particular flighting plate 37. The first warning may include a visual indication (e.g., using words, letters, numbers, flashing lights, etc.) that a component replacement is required. In some embodiments, the first warning may be a general warning indicating a fighting plate 37 should be replaced. In other embodiments, controller 66 may help identify the particular flighting plate 37 that should be replaced, for example by communicating a unique identifier of the component and/or a position on milling drum 16 of where the component should be located.

Controller 66 may determine the location of the damaged component on milling drum 16 based on a strength of signals generated by the associated transmitter(s) before damage occurred. Controller 66 may store the location within its memory and access the stored location when generating the first warning. Controller 66 may be configured to show or otherwise communicate the first warning and/or the location of the component to the operator of cold planer 10 via display 30.

Controller 66 may be also be configured to determine when each component of milling drum 16 exceeds its wear threshold based on the signals emitted by the associated transmitter(s). For example, any time reader 62 stops detecting the signal from transmitter 44 associated with top portion 82 of tool holder 33, but still is able to detect the signal emitted by transmitter 46 associated with middle portion 84 of tool holder 33, controller 66 may determine that tool holder 33 is still connected to milling drum 16 and that only top portion 82 has worn away. Similarly, when the signal from transmitter 46 is also not detected, but the signal emitted by transmitter 48 associated with lower portion 86 of tool holder 33 is detected by reader 62, controller 66 may determine that both the top and middle portions 82, 84 have worn away. In this manner, controller 66 may rely on the same signals that are used to determine breakage to also indicate when a component of milling drum 16 wears beyond thresholds specified for the component. Thus, monitoring system 64 may be simplified in design and incur lower production costs, while being able to monitor multiple facets of each component of milling drum 16.

Controller 66 may be configured to generate a second warning when it determines that wear of a component of milling drum 16 has exceeded the associated wear threshold. The second warning may be indicative of a recommendation to inspect the component at the operator's next convenient opportunity. That is, when the component reaches the wear threshold, operation using the component may be able to continue for a period of time to allow for a more efficient overall milling operation. In particular, the operator may wish to continue the milling operation using a worn component until a more convenient opportunity arises to fully stop the milling operation, such as during a shift break, a shift change, when an empty transport truck is approaching, at the end of the day, etc. At such a time, the operator may be able to inspect the worn component and determine whether to replace it immediately or to allow continued operation. In this way, a life of the component may be extended, thereby partially reducing the overall cost of the milling operation. Alternatively or additionally, the second warning may be used as a reminder to order a replacement component before complete failure of the component.

Controller 66 may be configured to show the second warning to the operator via display 30. For example, the second warning may include a visual indication (e.g., using words, letters, numbers, flashing lights, etc.) that the component has exceeded the wear threshold and should be inspected. Like the first warning described above, the second warning may be a general warning that a particular type of component (e.g., a fighting or a paddle) should be inspected. In other embodiments, controller 66 may help identify the exact component that is worn by communicating the unique identification signal of transmitter(s) associated with the component. As described with regard to the first warning, controller 66 may be configured to communicate a location of the component with the second warning to facilitate a speedy replacement.

To help operators and worksite managers plan inspections of milling drum 16 and to better assess the costs associated with operating cold planer 10, controller 66 may be configured to track a time elapsed $T_E$ after a component of milling drum 16 is connected to milling drum 16 until it exceeds the wear threshold or should be replaced. For example, controller 66 may begin tracking the time elapsed $T_E$ after the component is connected to milling drum 16, and record a current date and/or time within its memory (e.g., via an electronic timestamp). The elapsed time $T_E$ and/or timestamp may be recorded for each transmitter disposed within the component. The stored information may be then be analyzed to determine whether particular components will soon need to be changed, even though the transmitters associated with those components may still be emitting signals.

When the signal emitted by a respective transmitter stops being detected by reader 62 (e.g., when a first or second warning is generated), controller 66 may be configured to record the elapsed time $T_E$ and/or timestamp and associate it with the unique identification signal emitted by the respective transmitter. In this way, controller 66 may store in its memory the elapsed time $T_E$ and/or specific time at which each transmitter stops being detected. Controller 66 may also record the type of warning that is generated, and associate the unique identification signal with the type of warning. In this way, controller 66 may store information about the failure mode of a particular component and used to assess the performance of a particular component (make, model, etc.), a machine, and/or an operator of milling drum 16.

In some embodiments, controller 66 may also be configured to determine an operational lifespan and/or a remaining life of a component of milling drum 16 based on the elapsed time $T_E$ after the component was connected to milling drum 16. For example, monitoring system 64 may include any number of sensors 72 disposed throughout cold planer 10. Sensors 72 may be configured to generate signals indicative of machine operating parameters, such as a rotational speed ω of milling drum 16, a depth D of milling drum 16 below work surface 22, a ground speed V of cold planer 10, and/or other parameters. Controller 66 may be configured to associate the elapsed time $T_E$ with at least one sensed parameter to determine an amount of time that the component was actually in engagement with work surface 22 to thereby determine a work time $T_w$ of the component. For instance, when the rotational speed ω, depth D, and/or ground speed V of cold planer 10 have non-zero values, the component may be considered to be engaged with work surface 22 and experiencing wear. Based on the elapsed time $T_E$ and a typical life span known for the same component, the remaining useful life of the component may be determined (e.g., as a difference function). It is understood that other ways of determining when a component of milling drum 16 is engaged with work surface 22 may be possible.

Controller 66 may be configured to associate the work time $T_w$ of a component with the unique identification signal emitted by a respective transmitter each time the signal stops being detected by reader 62 (e.g., when a first or second warning is generated). In this way, controller 66 may be able to determine and record how long the component was (and can be) used during operation before it exceeded (or will exceed) the wear threshold, break off, break away, etc. The work time $T_w$ may be regarded as the lifespan of the component either when the component exceeds the wear threshold or when it ultimately fails or is removed (i.e., when reader 62 no longer detects the signal emitted by the transmitter within the component). This data may be stored within the memory of controller 66 and analyzed to determine operating costs and productivity of cold planer 10.

INDUSTRIAL APPLICABILITY

The disclosed wear monitoring system may be used with any cold planer where detecting the loss and/or wearing out of a component of the milling drum is important. The disclosed monitoring system may determine when each component is connected to the milling drum, when it exceeds a wear threshold, and/or when it breaks or falls out of the milling drum based on signals transmitted from within the component. The system may provide warnings to an operator each time a component wears out or is no longer detected, and also record the lifespan and failure mode of each component for future cost and productivity analysis. Operation of monitoring system 64 will now be explained.

When cold planer 10 is at rest (e.g., before a milling operation starts, during a break in the operation, etc.), a new component, for example base block 35, may be connected to milling drum 16. When the milling operation is resumed, reader 62 may detect the signal generated by at least one transmitter disposed within the new component (e.g., by transmitter 52). Each signal may be unique and identify the associated component. Upon detection of each signal, controller 66 may record each respective identification within its memory and begin to track the time elapsed $T_E$ since connection of the new component. Controller 66 may also record a timestamp upon detection of each signal, and associate the elapsed time $T_E$ and timestamp with the respective identification signal.

During operation, the new component may engage work surface 22 (and/or material torn from work surface 22). Controller 66 may determine when the component is engaged with work surface 22 based on signals generated by sensors 72. Controller 66 may continually track the elapsed time $T_E$ in coordination with the parameters measured by sensors 72, and responsively determine a work time $T_w$ of the new component. Controller 66 may store the work time $T_w$ within its memory for use during future processing.

As operation of cold planer 10 continues, controller 66 may monitor the signals generated by each transmitter disposed within the new component. Controller 66 may generate a warning when one or more of the signals generated by the respective transmitter(s) are lost (i.e., when the signal(s) stop being detected by reader 62). For example, when each transmitter 52 has been damaged, worn, or broken away, reader 62 may no longer be able to detect signals from particular transmitters (e.g., from transmitter 52 of the new base block 35). When reader 62 no longer detects the signal from transmitter 52, controller 66 may determine that base block 35 should be replaced and generate a first warning. The first warning may be indicative of a recommendation to replace the component at the operator's earliest convenience. Controller 66 may show the first warning to the operator via display 30.

As long as a signal emitted by a particular transmitter associated with the component is detected by reader 62 during operation of cold planer 10, controller 66 may determine that the component is still connected to milling drum 16. When a component includes more than one transmitter, and the signals from fewer than all of the transmitters are lost, controller may determine that at least a portion of the component has exceeded a wear threshold. Controller 66 may then generate a second warning and show it to the operator via display 30. The second warning may be indicative of a recommendation to inspect the component at the operator's next convenient opportunity.

Each time the first and/or second warning is generated, controller 66 may record the elapsed time $T_E$, timestamp, the type of warning that was generated (e.g., the first or second warning), and the work time $T_w$ into its memory. This data may be associated with the unique identification signal that was lost (that is not longer detected by reader 62). The work time $T_w$ recorded by controller 66 may then be regarded as the lifespan of the component.

During operation, controller 66 may determine where on milling drum 16 a component is located (e.g., based on the strength of the signal emitted by transmitters) and store the location in its memory (e.g., in association with the ID of the respective signal). Each time the first and/or second warning is generated, controller 66 may then communicate the stored location of the respective component to the operator via display 30. In this way, the operator of cold planer 10 may be quickly notified when the component should be replaced to avoid reductions in milling quality and/or further damage to milling drum 16.

Several advantages may be associated with the disclosed monitoring system. For example, because controller 66 may determine whether a component of milling drum 16 is connected to milling drum 16 and also when the same component reaches a wear threshold based on the same signals emitted by the same transmitter(s), monitoring system 64 may be simple and inexpensive to implement. Further, because the same transmitter(s) may be used to indicate multiple facets of component life, fewer transmitters may be required. This may help to reduce the void spaces within each component and thereby improve a durability of the component. Additionally, because controller 66 may generate warnings when a component exceeds a wear threshold and when the component is not connected to milling drum 16, operators may be allowed to decide when it is most convenient and cost effective to replace the component. Controller 66 may provide data about the lifespan of a component of milling drum 16 that can be used to plan more efficient milling operations in the future.

It will be apparent to those skilled in the art that various modifications and variations can be made to the disclosed monitoring system without departing from the scope of the disclosure. Other embodiments of the monitoring system will be apparent to those skilled in the art from consideration of the specification and practice of the monitoring system disclosed herein. It is intended that the specification and examples be considered as exemplary only, with a true scope of the disclosure being indicated by the following claims and their equivalents.

What is claimed is:

1. A milling drum, comprising:
   a cylindrical body;
   a flighting plate affixed to an outer surface of the cylindrical body;
   a base block affixed to the flighting plate and having a first bore;
   a tool holder disposed in the first bore of the base block and having a second bore;
   a cutting tool disposed in the second bore of the tool holder;
   a paddle affixed to the outer surface of the cylindrical body adjacent the flighting plate;
   a first transmitter coupled to the cutting tool; and
   a second transmitter coupled to the tool holder, wherein each of the transmitters is configured to emit a unique identification signal that is associated with a respective corresponding component of the milling drum such that a controller receiving a respective one of the signals can identify a particular component in need of replacement or repair by loss of the respective one of the signals, and determine a location of the particular component from a strength of the respective one of the signals, and wherein the controller is configured to record a time elapsed from when the particular component was first installed on the milling drum based on a time when the controller first receives the respective one of the signals to when the particular component is in need of replacement or repair and associate the time elapsed with a sensed operating parameter of the milling drum to determine a total work time for the particular component and a remaining useful life for the particular component by calculating a difference between the total work time and a recorded typical life span for the particular component.

2. The milling drum of claim 1, further including a third transmitter coupled to the base block.

3. The milling drum of claim 2, further including a fourth transmitter coupled to the flighting plate.

4. The milling drum of claim 3, further including fifth transmitter coupled to the paddle.

5. The milling drum of claim 1, wherein:
   the tool holder includes a plurality of segments that are exposed after assembly into the first bore of the base block; and
   the second transmitter is coupled to a first of the plurality of segments that is closest to the base block.

6. The milling drum of claim 5, further including at least a third transmitter coupled to another of the plurality of segments of the tool holder.

7. A wear monitoring system for a milling drum having a flighting plate affixed to an outer surface of a cylindrical body of the milling drum, a base block affixed to the flighting plate, a tool holder connected to the base block, a cutting tool connected to the tool holder, and a paddle affixed to the outer surface of the cylindrical body adjacent the flighting plate, the wear monitoring system comprising:
   a first transmitter configured to emit a first signal indicative of a status of the cutting tool;
   a second transmitter configured to emit a second signal indicative of a status of the tool holder;
   a reader configured to receive the first and second signals;
   a display; and
   a controller in communication with the reader and the display, and configured to:
      selectively cause the display to show a wear status and a connection status of the cutting tool based on a loss of the first signal;
      selectively cause the display to show a wear status and a connection status of the tool holder based on a loss of the second signal, wherein each of the transmitters is configured to emit a unique identification signal that is associated with a respective corresponding component of the milling drum such that the controller receiving a respective one of the signals can identify a particular component in need of replacement or repair and determine a location of the particular component from a strength of the respective one of the signals;
      record a time elapsed from when the particular component was first installed on the milling drum based on a time when the controller first receives the respective one of the signals to when the particular component is in need of replacement or repair;
      associate the time elapsed with a sensed operating parameter of the milling drum to determine a total work time for the particular component; and
      determine a remaining useful life for the particular component by calculating a difference between the total work time and a recorded typical life span for the particular component.

8. The wear monitoring system of claim 7, further including a third transmitter configured to emit a third signal indicative of a status of the base block, wherein:
   the reader is further configured to receive the third signal; and
   the controller is further configured to selectively cause the display to show a wear status and a connection status of the base block based on loss of the third signal.

9. The wear monitoring system of claim 8, wherein the controller is further configured to generate a warning indicative of a recommendation to replace the base block based on loss of the third signal.

10. The wear monitoring system of claim 8, further including a fourth transmitter configured to emit a fourth signal of indicative of a status of the flighting plate, wherein:
the reader is further configured to receive the fourth signal; and
the controller is further configured to selectively cause the display to show a wear status and a connection status of the flighting plate based on loss of the fourth signal.

11. The wear monitoring system of claim 10, wherein the controller is further configured to generate a warning indicative of a recommendation to replace the flighting plate based on loss of the fourth signal.

12. The wear monitoring system of claim 10, further including a fifth transmitter configured to emit a fifth signal indicative of a status of the paddle, wherein:
the reader is further configured to receive the fifth signal; and
the controller is further configured to selectively cause the display to show one of a wear status and a connection status of the paddle based on loss of the fifth signal.

13. The wear monitoring system of claim 12, wherein the controller is further configured to generate a warning indicative of a recommendation to replace the paddle based on loss of the fifth signal.

14. The wear monitoring system of claim 8, wherein the controller is further configured to:
cause the display to show a remaining life of the tool holder based on the second and third signals; and
cause the display to show a lifespan of the tool holder based on the third signal.

15. The wear monitoring system of claim 7, wherein:
the tool holder includes a plurality of exposed segments;
the second transmitter is associated with a first of the plurality of segments that is closest to the base block;
the wear monitoring system further includes at least a third transmitter coupled to another of the plurality of exposed segments and configured to generate a third signal indicative of a status of the tool holder;
the reader is further configured to receive the third signal; and
the controller is configured to cause the display to show the connection status of the tool holder based on loss of both the second and third signals, and to show the wear status of the tool holder based on loss of only the third signal.

16. The wear monitoring system of claim 15, wherein the controller is further configured to cause the display to show a recommendation to inspect the tool holder based on the wear status.

17. The wear monitoring system of claim 16, wherein the controller is further configured to cause the display to show a recommendation to replace the tool holder based on the connection status.

18. A method of monitoring wear of a milling drum having a flighting plate affixed to an outer surface of a cylindrical body of the milling drum, a base block affixed to the flighting plate, a tool holder connected to the base block, a cutting tool connected to the tool holder, and a paddle affixed to the outer surface of the cylindrical body adjacent the flighting plate, the method comprising:
detecting a flighting plate signal;
detecting a base block signal;
detecting a tool holder signal;
detecting a cutting tool signal;
selectively displaying a wear status and a connection status of the flighting plate, the base block, the tool holder, and the cutting tool based on loss of the flighting plate signal, the base block signal, the tool holder signal, and the cutting tool signal, wherein each of the signals is a unique identification signal that is associated with a respective corresponding component of the milling drum such that a controller receiving a respective one of the signals can identify a particular component in need of replacement or repair by loss of the respective one of the signals, and determine a location of the particular component from a strength of the respective one of the signals;
recording, with the controller, a time elapsed from when the particular component was first installed on the milling drum based on a time when the controller first receives the respective one of the signals to when the particular component is in need of replacement or repair;
associating, with the controller, the time elapsed with a sensed operating parameter of the milling drum to determine a total work time for the particular component; and
calculating, with the controller, a difference between the total work time and a recorded typical life span for the particular component to determine a remaining useful life for the particular component.

19. The method of claim 18, wherein:
detecting the tool holder signal includes detecting a first tool holder signal and a second tool holder signal transmitted from different exposed segments of the tool holder;
selectively displaying a wear status and a connection status the tool holder includes:
displaying the connection status based on loss of the first and second tool holder signals; and
displaying the wear status based on loss of only one of the first and second tool holder signals.

20. The method of claim 18, further including determining at least one of a remaining life and a lifespan of the flighting plate, the base block, the tool holder, and the cutting tool based on the flighting plate signal, the base block signal, the tool holder signal, and the cutting tool signal.

* * * * *